(12) United States Patent  
O'Mahoney

(10) Patent No.: US 6,321,748 B1
(45) Date of Patent: Nov. 27, 2001

(54) CLOSED LOOP CONTROL IN A PISTON VENTILATOR

(75) Inventor: John O'Mahoney, Carlsbad, CA (US)

(73) Assignee: Nellcor Puritan Bennett, Pleasanton, CA (US)

( * ) Notice: Subject to any disclaimer, the term of this patent is extended or adjusted under 35 U.S.C. 154(b) by 0 days.

(21) Appl. No.: 09/037,385

(22) Filed: Mar. 10, 1998

(51) Int. Cl.$^7$ .................................................. A61M 16/00
(52) U.S. Cl. ................... 128/204.21; 128/204.23
(58) Field of Search .................. 128/204.18, 204.21, 128/204.23, 205.18

(56) References Cited

U.S. PATENT DOCUMENTS

| 4,587,967 | * | 5/1986 | Chu et al. | 128/205.18 |
| 4,617,637 | * | 10/1986 | Chu et al. | 128/205.18 |
| 4,726,366 | * | 2/1988 | Apple et al. | 128/205.18 |
| 4,957,107 | * | 9/1990 | Sipin | 128/204.21 |
| 5,107,830 | | 4/1992 | Younes | 128/204.18 |
| 5,540,222 | | 7/1996 | Younes | 128/20 |
| 6,076,523 | * | 6/2000 | Jones et al. | 128/204.21 |

FOREIGN PATENT DOCUMENTS

WO 9624402   8/1996   (WO).

* cited by examiner

Primary Examiner—Aaron J. Lewis
(74) Attorney, Agent, or Firm—Hovey, Williams, Timmons & Collins

(57) ABSTRACT

A piston ventilator (10) includes a control circuit (80) for controlling the pressure to a patient circuit and thereby to the patient during patient inspiration. The control circuit (80) determines an error between the gas pressure and a set point pressure and in response, sends motor control signals to the motor (24) controlling the piston (22) to change the gas flow therefrom by the amount necessary so that the gas pressure substantially conforms to the set point pressure. More particularly, the motor control signals are a function of a proportion of the error, an integration of the error and the amount of leakage in the patient circuit at the current gas pressure. The set point is one of a plurality of set points on a pressure trajectory between a beginning pressure and a final target pressure during patient inspiration.

6 Claims, 5 Drawing Sheets

CLOSED LOOP CONTROL IN A PISTON VENTILATOR

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention deals with the field of piston ventilators for patients in need of respiratory assistance. More particularly, the invention is concerned with a control circuit for a piston ventilator that corrects for errors in the gas pressure delivered to the patient compared to a set point pressure by taking into account the error magnitude, the integration of the error over time and gas leakage in the system. The control circuit also determines the set point pressure as one of a plurality of sequential set point pressures on a pressure trajectory during patient inspiration.

2. Description of the Prior Art

The prior art discloses control devices for piston ventilators in which analog signals representative of motor current and desired current are compared to generate an analog error signal. The error signal is used to drive the piston motor in order to minimize the error. In the prior art, a brushed DC motor was used. The relationship between current and torque, i.e., the torque constant for a DC motor, was used to generate specific pressures. Specifically, torque equals force times distance, therefore, for a given torque on a piston, a particular pressure could be generated.

These prior art control schemes present a number of problems. For example, the torque constant varies with temperature. As a result, the error is never eliminated in a controlled fashion. The prior art uses current control which is a function of how frictionless the piston is. Moreover, the signals delivered to the piston motor do not take into account gas leaks in the system. Also, the prior art analog control schemes do not provide the desired level of precision and flexibility in operation needed for medical applications.

SUMMARY OF THE INVENTION

The present invention solves the prior art problems discussed above and provides a distinct advance in the state of the art. More particularly, the piston ventilator of the present invention uses digital processing to implement a control scheme for eliminating error between actual pressure in the patient circuit and the set point pressure.

The preferred piston ventilator includes a pressure sensor, a motor controller and a digital processor under software control. The processor receives sensor signals from the pressure sensor representative of the actual gas pressure in the patient circuit of the ventilator. In response, the processor determines the gas flow amount from the piston necessary so that the actual gas pressure substantially conforms to a predetermined set point pressure, and delivers motor control signals representative of the gas flow amount to the motor controller.

In preferred forms, the set point pressure is one of a plurality of sequential set point pressures on a pressure trajectory. This trajectory is determined as a function of a predetermined rate of rise as set by the user between a beginning pressure and a target pressure. The beginning pressure is the pressure in the patient circuit at the beginning of patient inspiration and is typically the PEEP pressure (positive expiratory exhalation pressure).

In other preferred aspects of the invention, the motor control signals are a function of the error between the set point pressure and actual gas pressure. More particularly, the motor control signals are a function of the sum of a proportional constant times the error, an integration constant times the error over time, and a leak constant times the actual pressure.

DETAILED DESCRIPTION OF THE PREFERRED EMBODIMENT

Figure 1:
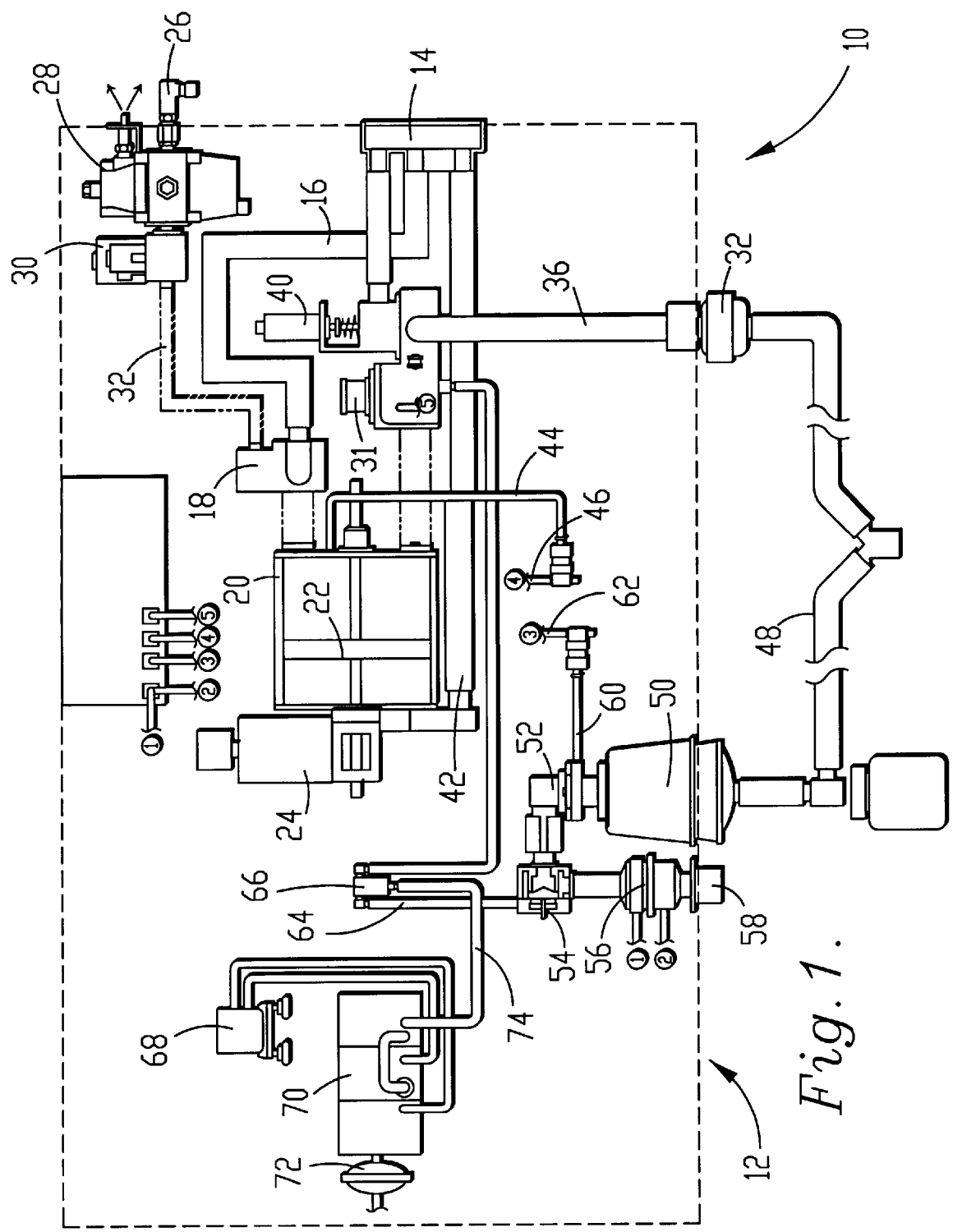
FIG. 1 is a diagram of the pneumatic system of the preferred piston ventilator in accordance with the present invention.

FIG. 1 illustrates preferred ventilator 10 in accordance with the present invention. More particularly, FIG. 10 illustrates pneumatic system 12 of the ventilator. Pneumatic system 12 broadly includes inhalation components, exhalation components, and the PEEP components.

The piston inhalation components include air intake filter 14, intake line 16 and mixing manifold 18 connected to the check valve inlet of cylinder 20 containing piston 22 driven by piston motor 24. The piston air intake components further include oxygen fitting 26, oxygen regulator 28, oxygen solenoid 30 and oxygen inlet line 32 connected with manifold 18 for mixing oxygen with ambient air received through filter 14. As such, the mixture is the gas delivered to the patient by ventilator 10. The check valve outlet of cylinder 20 is connected to oxygen sensor 31. Inhalation line 36 interconnects oxygen sensor 31 with the patient by way of the inspiratory filter 32. Safety valve 40 is connected to line 36 adjacent sensor 31. The inhalation components also include line 42 for exhausting air from cylinder 20 during retraction of piston 22. Line 44 interconnects cylinder pressure transducer 46 (Pcyl) with cylinder 20 on the discharge side of piston 22.

The exhalation components include exhalation line 48 connected with the patient thereby common with inhalation line 36. Exhalation line 48 connects to expiratory filter 50 and from there through heater assembly 52, exhalation valve 54 and exhalation flow sensor 56 to exhaust outlet 58. The exhalation components also include line 60 interconnecting exhalation pressure transducer 62 (Pexp) with expiratory filter 50. Line 64 interconnects exhalation solenoid 66 with exhalation valve 54.

The PEEP components include PEEP pump 68 connected as shown to PEEP reservoir 70, which receives inlet air through filter 72. Line 74 connects reservoir 70 with exhalation solenoid 66.

Figure 2A:
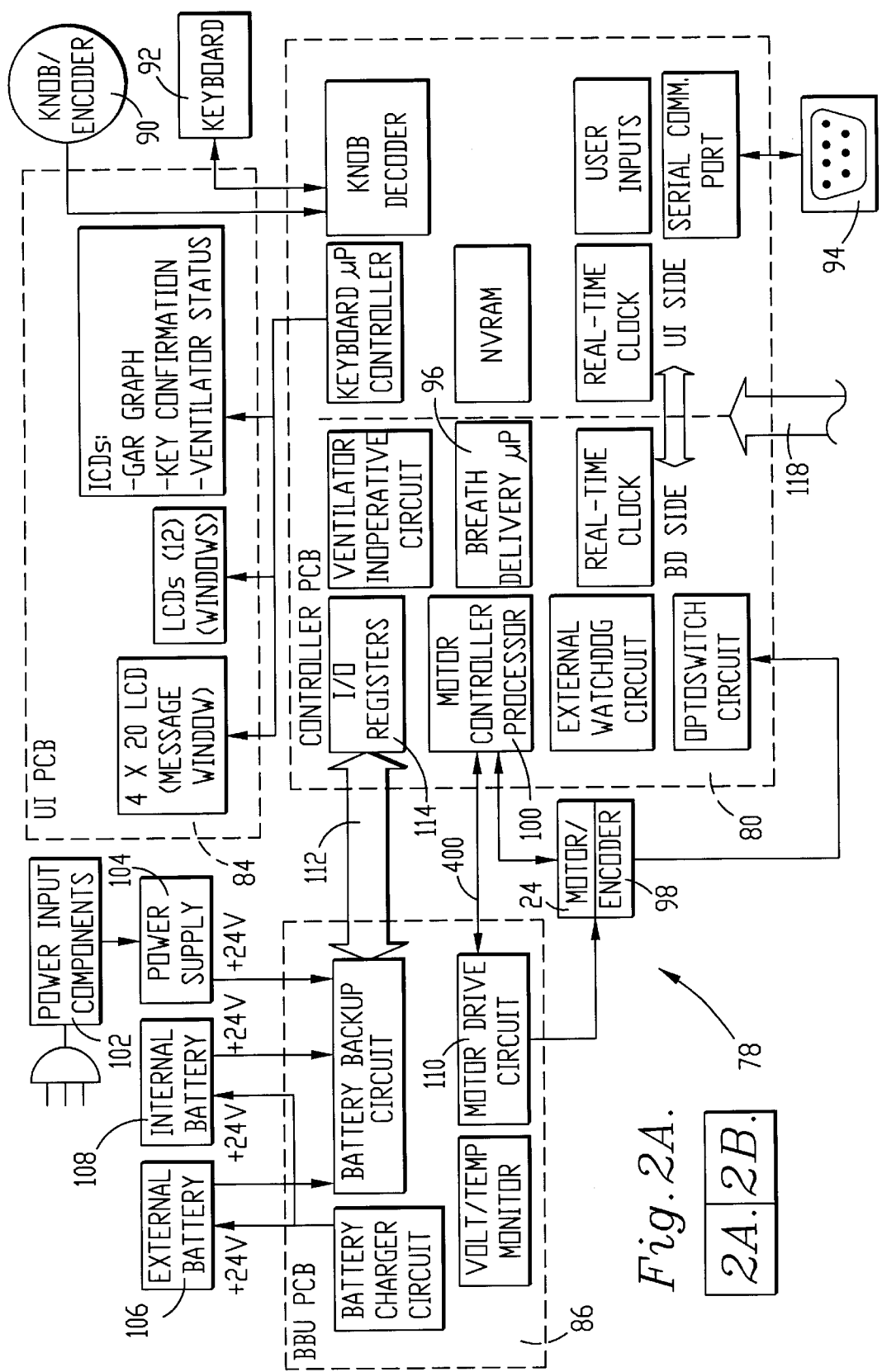
FIG. 2A is an electrical diagram illustrating a first portion of the electrical system of the ventilator of FIG. 1.
Figure 2B:
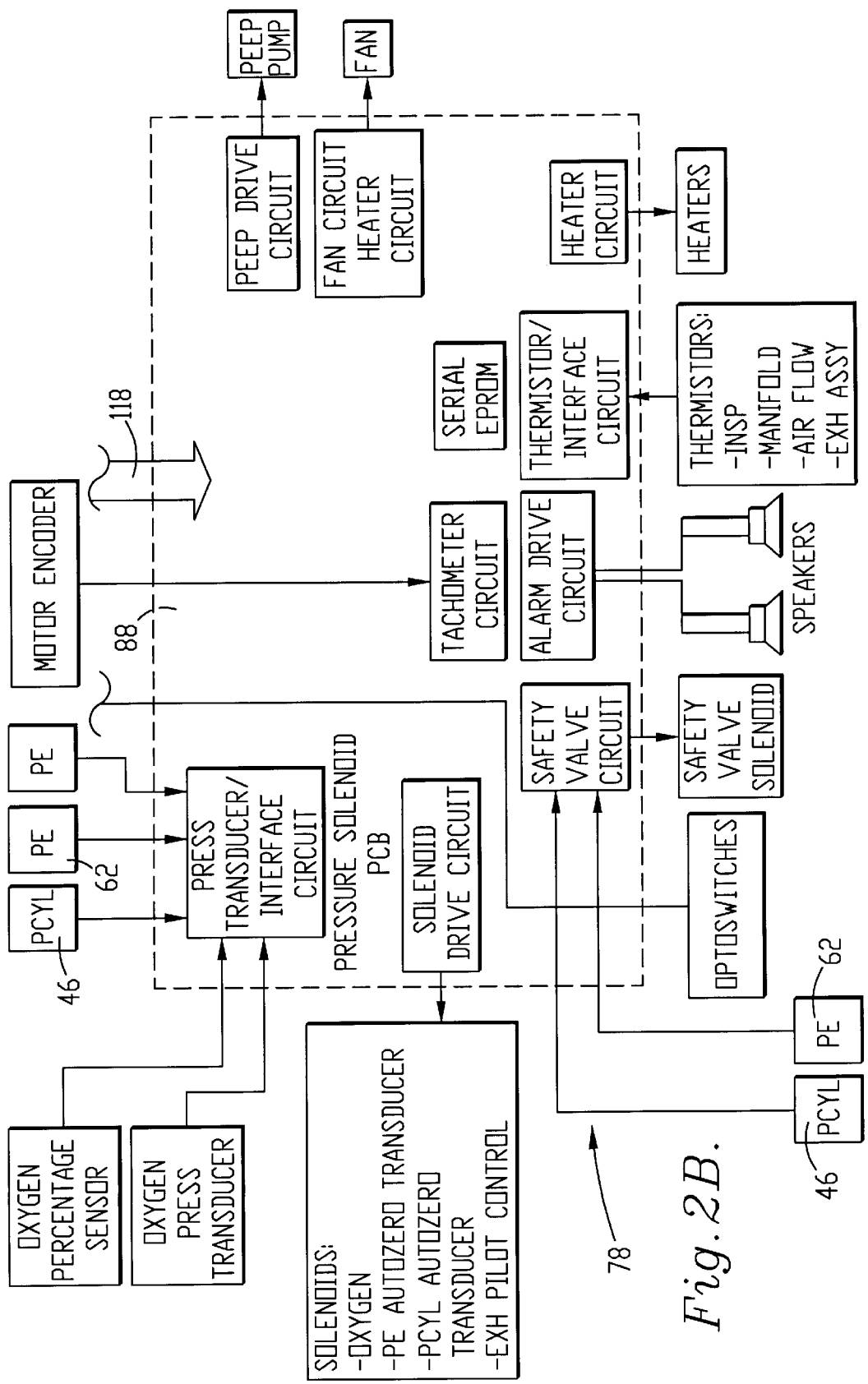
FIG. 2B is an electrical diagram illustrating the second portion of the electrical system of the ventilator of FIG. 1.

FIGS. 2A and 2B illustrate the electrical system 78 for operating ventilator 10. Electrical system 78 broadly includes main control circuit 80, display circuit 84 and motor controller 86 as illustrated in FIG. 2A, and solenoid circuit 88 illustrated in FIG. 2B.

Main control circuit 80 includes the components labeled therein and interconnects with components 82–88 as shown. In addition, main control circuit 80 receives inputs from knob encoder 90 for entering inspiration target pressure, PEEP pressure, pressure rise time during inspiration, and breath timing when in the pressure control mode. Main control circuit 80 is also connected with keyboard 92 and serial port 94.

Main control circuit 80 further includes a digital processor in the nature of breath delivery microprocessor 96 under control of a computer program stored therein. Microprocessor 96 receives inputs from motor controller microprocessor 100 representative of the position and movement of piston motor 24 by way of motor controller interface 100 and encoder 98.

Display circuit 84 receives data from main control circuit 80 for providing the various displays indicated in FIG. 2A.

Motor controller 86 receives operating power from a conventional household supply by way of power input components 102 and power supply 104. Motor controller 86 is also connected to external battery 106 and internal battery 108 that provide backup power in the event of external supply disruption. Motor drive circuit 110 connects with piston motor 24 and drives motor 24 in accordance with the motor control signals received over bus 400 from motor controller microprocessor 100 (114).

As illustrated in FIG. 2B, solenoid circuit 88 operates as the control interface for the various solenoids and transducers. Specifically, circuit 88 receives inputs from exhalation pressure transducer 62 and cylinder transducer 46. These transducers function as pressure sensors coupled with the patient circuit for indicating the pressure therein. The sensor signals representative thereof are converted to analog sensor signals in interface circuit 116. These analog sensor signals are transmitted by way of bus 118 to main control circuit 80 as input to breath delivery microprocessor 96 where the signals are converted to digital.

Figure 3:
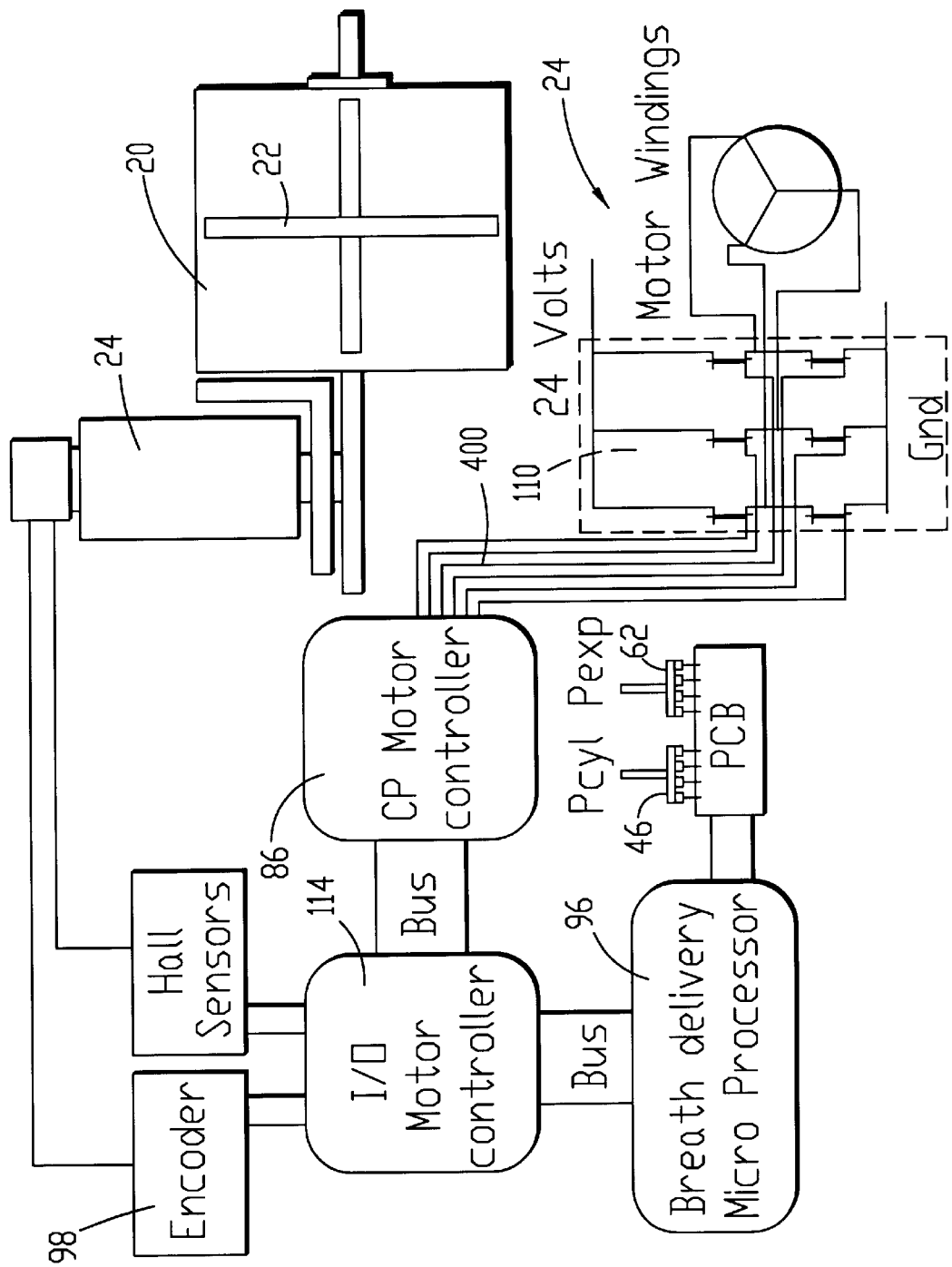
FIG. 3 is a block diagram illustrating the preferred control circuit shown coupled with the piston motor and pressure sensors of the ventilator of FIG. 1.

FIG. 3 is a simplified block diagram showing selected components from FIGS. 1, 2A and 2B used in controlling the operation of piston motor 12 and thereby piston 22 and the pressure in the patient circuit. In general, the patient circuit includes those pneumatic passages of ventilator 10 in communication with the patient.

In operation, breath delivery microprocessor 96 as the preferred digital processor receives sensor signals from cylinder pressure transducer (Pcyl) 46 and exhaust pressure transducer (Pexp) 62. In response, microprocessor 96 provides motor control signals to motor controller 86 by way of I/O register 114. In response to the motor control signals, motor controller activates piston motor 24 and the windings thereof in order to drive piston 22 for delivering gas to the patient circuit at a gas pressure and flow. Motor encoder 98 provides motor position signals to microprocessor 96 by way of I/O register 114.

Figure 4:
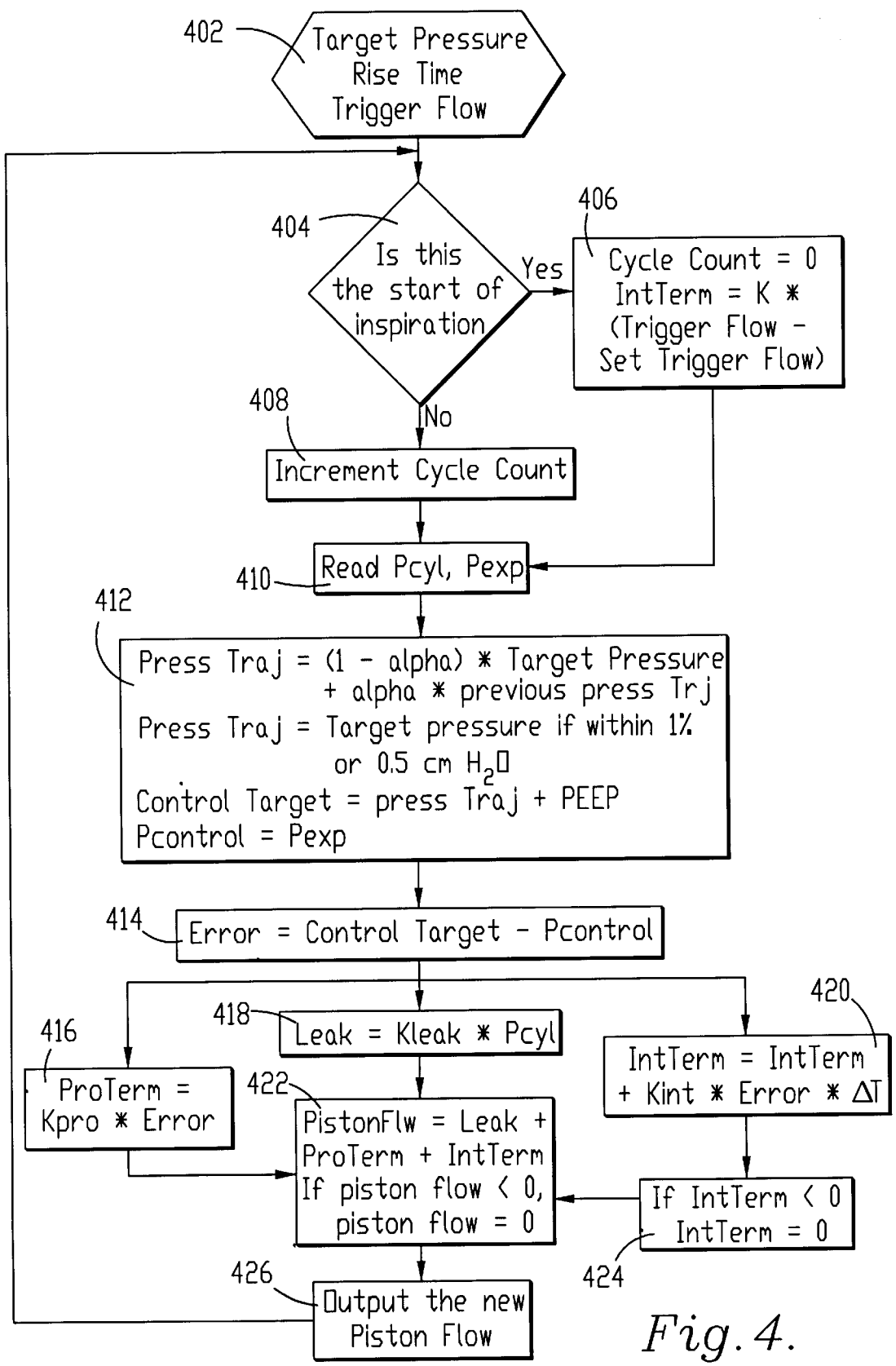
FIG. 4 is a flow chart illustrating the preferred computer program for operating the control circuit of FIG. 3.

FIG. 4 is a flow chart of pertinent portions of the preferred computer program for controlling the operation of microprocessor 96 in order to control the operation of piston motor 24. FIG. 4 illustrates operation in the pressure control ventilation mode where the initiation of a breath is on a timed basis. The present invention is also useful in the pressure support mode in which the onset of patient inspiration may trigger ventilator 10 to provide pressurized gas in the patient circuit to assist inspiration.

The program illustrated in FIG. 4 enters at step 402 and retrieves initialization data from the nonvolatile random access memory (NVRAM) illustrated in FIG. 2A. This initialization data includes the target pressure during patient inspiration, the rise time for the increase in the pressure in the patient circuit during patient inspiration, and the trigger flow which is the flow in the patient circuit indicating the onset of patient inspiration.

Step 404 then asks whether this pass through the program loop indicates the start of patient inspiration. If yes, step 406 sets the variable "cycle count" to zero, and sets the variable "integration term" (IntTerm) as equal to a constant K times the current trigger flow minus the set trigger flow.

If the answer in step 404 is no, indicating that this is not the first pass through the program loop, step 408 increments the cycle count variable. Next, step 410 reads the current pressure indicated by the sensor signals provided by transducers 46 and 62 as the variables Pcyl and Pexp.

Step 412 calculates the variable Press Traj which is the current pressure on a pressure trajectory or curve for the rise of the pressure during inspiration. As indicated, the variable Press Traj is a function of the constant alpha which is derived from the desired rise time for the gas pressure in the patient circuit. In particular, $$\text{alpha}=\exp(-1/\text{tau}-\Delta T)$$

wherein, $$\text{tau}=\text{rise time (in seconds)}/3$$

where the rise time is between 0 and 95% of target. This yields a value for alpha as 0.501 rounded to 0.5. A higher value for F yields a smaller value for alpha which results in a more rapid rise from the beginning pressure to the target pressure.

For example, if alpha is 0.5 and the target pressure is 10 cm water, then the first term in the equation for Press Traj is (1−0.5)×10 cm which equals 5 cm. The second term is zero because this is the first calculation for Press Traj. Accordingly, the initial set point pressure is 5 cm.

During the next pass through the program loop, the second term will be 2.5 cm (0.5×5 cm) and the new Press Traj will be 7.5 cm (5 cm+2.5 cm). On the third calculation, Press Traj will be 8.75 cm and, on the fourth, will be 9.375 cm, and so forth. Thus, each value of Press Traj is one of a plurality of points on the pressure trajectory or curve that reflects the desired rise time for the inspiration pressure.

As will be appreciated, the value of Press Traj approaches the target pressure in the limit. However, if Press Traj is within 1% or with 0.5 cm water of the target pressure, whichever is greater, then Press Traj is set equal to the target pressure.

Step 412 next determines the control target, or current set point pressure, as the value of Press Traj plus the PEEP pressure. That is, the PEEP pressure is already present in the patient circuit at the beginning of inspiration. The target pressure is the increase in pressure delivered to the patient circuit. Finally, step 412 sets the variable Pcontrol equal to Pexp, which is the current pressure in the patient circuit as measured by transducer 62.

Step 414 calculates the error as the difference between actual pressure (Pcontrol) in the patient circuit and the current set point pressure (Control Target). After the error is calculated, the task is to change the air flow in the patient circuit by the amount necessary to correct the error so that the gas pressure in the patient circuit substantially conforms to the set point pressure. To accomplish this, steps 416, 418, and 420 calculate the individual correction terms to be used in step 422.

Step 416 calculates the proportional term (ProTerm) as the error times a proportional constant (Kpro). The constant Kpro is empirically derived for ventilator 10 as being high enough to provide substantial correction without adding instability to the system.

Step 418 calculates the leak term for compensating for leakage in the system. The system leakage is substantially the amount of leakage between piston 22 and cylinder 20. The clearances between piston 22 and cylinder 20 are designed to reduce friction. In so doing, a certain amount of leakage is expected, and the leakage is proportional according to the constant Kleak to the pressure (Pcyl) in cylinder 20 as indicated by transducer 46.

Step 420 calculates an integration term (IntTerm) as the previous IntTerm plus an integration constant (Kint) times the error over time ($\Delta T$). The initial integration term is set in step 406 as discussed above. This term integrates the error over time so that the error can be eliminated. That is, if only proportional correction is used, the error is never specifically eliminated and can accumulate over time. The integration term corrects this problem. The time frame for $\Delta T$ is 10 ms, which is the sampling time used in the preferred embodiment.

Step 422 determines the gas flow amount (PistonFlw)as provided by piston 22 to the patient circuit necessary to correct the error according to the correction terms calculated in steps 416–420. Specifically, the variable PistonFlw is the sum of the three correction terms.

It will be noted, however, that in step 424, the integration term is set equal to zero if determined as less than zero in step 420. This can happen if the error is negative, that is, if the actual pressure is above the set point. In such cases, setting the integration term to zero precludes a calculation that the piston should reverse direction. Any overshoot is rapidly eliminated by the leakage around the piston.

Finally, step 426 provides motor control signals to motor controller 86. These motor controller signals represent the new gas flow amount to be produced by piston 22 for correcting the error. In other words, the motor control signals are representative of the gas flow amount necessary from piston 22 so that the actual gas pressure as measured by transducer 62 conforms substantially to the current set point (Control Target). Motor controller 86 responds to the motor controller signals from breath delivery microprocessor 96 (by way of I/O register 114) by operating motor 24 at the speed necessary so that piston 22 produces the needed gas flow amount for correcting the error. Encoder 98 provides confirmation of the current motor speed and thereby the current gas flow amount.

The program then loops from step 426 back to step 404. During the second and subsequent passes through the program loop, the answer in step 404 is no, and step 408 increments the cycle count variable. The program then repeats steps 410–426 for the balance of patient inspiration.

Those skilled in the art will appreciate that the present invention encompasses many variations in the preferred embodiment described herein.

Having thus described this embodiment, the following is claimed as new and desired to be secured by Letters Patent:

1. In a piston ventilator having a piston motor for driving a piston to deliver gas at a gas pressure and flow to a patient circuit, a control circuit comprising:

a pressure sensor coupled with the patient circuit and operable for sensing the gas pressure therein and for producing sensor signals representative thereof;

a motor controller coupled with the piston motor for receiving motor control signals and for operating the piston motor in accordance therewith; and a digital processor under computer program control coupled with said motor controller and coupled with said pressure sensor for receiving and processing said pressure signals for determining the gas flow amount from said piston necessary so that said gas pressure substantially conforms to a predetermined set point pressure, and for producing motor control signals representative of said gas flow amount and delivering said motor control signals to said motor controller for driving said piston to produce said gas flow amount, said digital processor being programmed to determine said set point pressure as one of a plurality of sequential set point pressures on a pressure trajectory determined as a function of a predetermined rate of rise between a beginning pressure and a target pressure wherein said beginning pressure is the pressure in the patient circuit at the beginning of patient inspiration.

2. The control circuit as set forth in claim 1, said digital processor being programmed to determine an error as the difference between said set point pressure and said gas pressure and for producing said motor control signals as a function of a proportion constant times said error.

3. The control circuit as set forth in claim 1, said digital processor being programmed to determine an error as the difference between said set point pressure and said gas pressure, and for producing said motor control signals as a function of an integration constant times said error over time.

4. The control circuit as set forth in claim 1, said digital processor being programmed to determine an error as the difference between said set point pressure and said gas pressure, and for producing said motor control signals as a function of the sum of a proportion constant times said error and integration constant times said error over time.

5. The control circuit as set forth in claim 4, the patient circuit being subject to gas leakage proportional to the gas pressure, said sum further including a leak constant times a gas pressure.

6. The control circuit as set forth in claim 1, said digital processor including a microprocessor.

* * * * *